United States Patent
Kuo et al.

(10) Patent No.: US 6,737,272 B2
(45) Date of Patent: May 18, 2004

(54) METHODS FOR MODULATION OF OOCYTE ACTIVATION

(75) Inventors: Richard Kuo, Fremont, CA (US); Gregory Baxter, Ithaca, NY (US); David Epel, Carmel, CA (US)

(73) Assignees: The Board of Trustees of the Leland Stanford Junior University, Palo Alto, CA (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/733,266

(22) Filed: Dec. 8, 2000

(65) Prior Publication Data

US 2002/0106360 A1 Aug. 8, 2002

Related U.S. Application Data (60) Provisional application No. 60/172,692, filed on Dec. 10, 1999.

(51) Int. Cl.[7] .............................. C12N 5/06; C12N 5/08
(52) U.S. Cl. ..................... 435/375; 435/325; 435/366; 435/455
(58) Field of Search ................... 435/375, 325, 435/366, 455

(56) References Cited

U.S. PATENT DOCUMENTS

| | | | |
|---|---|---|---|
| 6,040,340 A | 3/2000 | Chwalisz et al. | 514/503 |
| 6,077,710 A | 6/2000 | Susko-Parrish et al. | 435/375 |
| 6,255,109 B1 * | 7/2001 | Hansel et al. | 435/373 |

OTHER PUBLICATIONS

Herrero et al. Reprod. Fertil. Dev., 1996, 8, pp. 301–302.*
Grumetto et al. Biochemical and Biophysical Research Communications. 1997. vol. 239, pp. 723–728.*
Jawerbaum et al. Reprod. Fertil. Dev.. 1997. vol. 9, No. 4, pp. 391–394.*
Berridge et al. (1998) "Calcium—a life and death signal." *Nature*, vol. 395:645–648.
Epel (1997) "Activation of sperm and egg during fertilization." In *Handbook of Physiology*, eds. Hoffman and Jamieson, Oxford University Press, New York, 859–884.
Stricker (1999) "Comparative Biology of Calcium Signaling during Fertilization and Egg Activation in Animals." *Developmental Biology*, vol. 211:157–176.

* cited by examiner

*Primary Examiner*—Vera Afremova
(74) *Attorney, Agent, or Firm*—James S. Keddie; Pamela J. Sherwood; Bozicevic, Field & Francis LLP (57) ABSTRACT

Nitric oxide synthase and nitric-oxide-related bioactivity are shown to be necessary and sufficient for activation of an oocyte during the process of fertilization. Methods are provided for the modulation of oocyte activation through modulation of nitric oxide levels. Oocyte activation is enhanced by the addition of nitric oxide synthase, nitric oxide synthase activators, nitric oxide donors, or other compounds that increase the nitric oxide levels of the oocyte during fertilization. The administration of NOS inhibitors is used to block oocyte activation, where contraception is desired.

6 Claims, 11 Drawing Sheets

```
                    SEQUENCE LISTING

<160> NUMBER OF SEQ ID NOS: 1

<210> SEQ ID NO 1
<211> LENGTH: 17
<212> TYPE: PRT
<213> ORGANISM: Rattus spe.

<400> SEQUENCE: 1

Thr Lys Arg Arg Ala Ile Gly Phe Lys Lys Leu Ala Glu Ala Val Lys
1               5                  10                  15

Cys
```

METHODS FOR MODULATION OF OOCYTE ACTIVATION

This application claims benefit of provisional application No. 60/172,692 filed Dec. 10, 1999.

STATEMENT REGARDING GOVERNMENT RIGHTS

This invention was supported at least in part by grant number IBN-9604353 from the National Science Foundation. The U.S. Government may have certain rights in the invention.

BACKGROUND OF THE INVENTION

In mammals, life begins at fertilization when the sperm interacts with the oocyte to trigger a series of intracellular $Ca^{2+}$ oscillations that persists for several hours. This prolonged period of repetitive $Ca^{2+}$ pulses triggers the developmental program by stimulating the enzymatic machinery involved in the cell division cycle. Further changes in intracellular $Ca^{2+}$ are not observed until the one cell embryo is ready to divide, when a spontaneous $Ca^{2+}$ transient triggers cleavage to form two daughter cells. The early steps that lead to the rises in calcium and oocyte activation at fertilization were unknown but of great interest, particularly with the advent of in vitro fertilization techniques, and whole-animal cloning by nuclear transfer. This calcium rise is required for oocyte activation and the subsequent events of development in eggs or oocytes of all species.

The meiotic division of mammalian oocytes begins with one primary germ cell (oocyte), which gives rise to only one mature ovum (egg). In normal mammalian development, oocytes become developmentally arrested in the ovaries at the germinal vesicle stage in prophase of the first meiotic division. Upon appropriate stimulation, meiosis resumes, the germinal vesicle breaks down, and the first meiotic division is completed with the extrusion of a diploid set of chromosomes into the first polar body, another diploid set of chromosomes remaining within the cytoplasm of the oocyte. The oocyte then becomes arrested at metaphase of the second meiosis ("Met II"). Met II oocytes (mature oocytes) can then be ovulated and fertilized.

Once fertilized, the activated oocyte completes the second meiotic division with the extrusion of a haploid set of chromosomes into the second polar body, male and female pronuclei are formed, and DNA replication is initiated in the pronuclei. The male and female pronuclei then fuse together, allowing their chromosomes to mingle. Equal segregation of the genetic material occurs by mitosis and the zygote cleaves to form two daughter blastomeres. The embryo continues to develop by undergoing a series of mitotic divisions before differentiating into specific cells, resulting in the organization of tissues and organs. This developmental program ensures the successful transition from oocyte to offspring.

When this process is defective, for example the inability of sperm to fertilize the egg, technical assistance has been sought. Since the first application of in vitro fertilization (IVF) in humans, the number of patients using assisted reproductive technologies (ART) has increased tremendously in number and technological spectrum. Infertility affects approximately one out of every six couples in the United States who desire children. For about 30% of couples male factor infertility will be the sole cause. An additional 20% will also have female factor infertility as an additional contributory factor. Therefore, a large percentage of infertility cases have a contributory male component.

Some options for dealing with male infertility include intracytoplasmic sperm injection (ICSI), which may use pre-ejaculate sperm for fertilization. The use of epididymal spermatozoa in assisted reproduction (ART) permits fertility in men with surgically irremediable obstructive azoospermia. However, when used for conventional IVF (sperm/oocyte co-culture), epididymal spermatozoa show reduced fertilization and pregnancy rates due to their functional immaturity. Part of this maturation occurs as the sperm cells move through the ducts of the male genital tract where fluid from the prostate gland and the seminal vesicles mix with the cells, forming the semen. Nevertheless, freshly ejaculated sperm are not yet capable of fertilizing an egg. The sperm must also go through the process of capacitation in the female genital tract that leads to release of enzymes that ultimately help the sperm penetrate an egg. Therefore, epididymal spermatocytes have an improved chance of fertility when combined with intracytoplasmic sperm injection (ICSI).

In addition to ICSI, nuclear transfer may have enormous applications in the fields of agriculture and biomedicine. This is especially true if a cell line that has been transformed can be used as a source of nuclei for the nuclear transfer and thus give rise to the cloning of an individual with an identical genetic composition as the transferred nucleus. One major aspect of the nuclear transfer and ICSI procedures is that of oocyte activation. Without oocyte activation the transferred nucleus would never progress to the first interphase. The inability to obtain development after artificial activation of oocytes has been a limiting factor in the application of these technologies. It is therefore of utmost importance that the oocyte be activated in a fashion that closely mimics the natural process which occurs at fertilization.

Improved methods of obtaining or preventing oocyte activation may find use with in vitro fertilization, nuclear transfer, contraception, and other reproductive technologies. The present invention addresses this issue.

Relevant Literature:

The role of calcium in biological signaling is reviewed by Berridge et al. (1998) *Nature* 395:645. The biology of egg activation is reviewed by Epel, in *Handbook of Physiology* (eds. Hoffman & Jamieson) 859–884 (Oxford Univ. Press, N.Y., 1997); and Stricker (1999) *Dev. Biol.* 211:157–176. Methods for parthenogenic oocyte activation are described in U.S. Pat. No. 6,077,710, Susko-Parrish et al.

The use of nitric oxide synthase modulators in enhancing implantation of embryos is discussed in U.S. Pat. No. 6,040,340, Chwalisz et al.

SUMMARY OF THE INVENTION

Methods are provided for the modulation of oocyte activation through modulation of nitric oxide levels. The invention is based on the finding that nitric oxide synthase and nitric oxide related bioactivity are necessary and sufficient for activation of an oocyte during the process of fertilization.

In one embodiment of the invention, oocyte activation is enhanced by the addition of nitric oxide synthase, nitric oxide synthase enhancers, nitric oxide donors, or other compounds that modulate the levels of nitric oxide in the oocyte during fertilization. The oocyte activation finds particular use in conjunction with artificial reproduction technologies, such as nuclear transfer, intracytoplasmic sperm injection, in vitro fertilization, and the like.

In another embodiment of the invention, the prevention of nitrosation of the oocyte, e.g. through the administration of NOS inhibitors, is used to block oocyte activation, where contraception is desired.

BRIEF DESCRIPTION OF THE DRAWINGS

FIGS. 1A to 1E depict NOS activity in *S. purpuratus* gametes.

FIGS. 2A to 2C depict nitric oxide changes after *S. purpuratus* gamete activation.

FIGS. 3A to 3C show that NO is necessary and sufficient for egg activation.

DETAILED DESCRIPTION OF THE EMBODIMENTS

Methods are provided for the modulation of oocyte activation through increasing or decreasing the activity of nitric oxide synthase (NOS). The invention is based on the finding that NOS and nitric-oxide-related bioactivity are necessary and sufficient for activation of an oocyte during the process of fertilization The methods of the invention demonstrate that exogenous NOS or nitrosation enhancing agents perform the same function in oocyte activation.

In one embodiment of the invention, oocyte activation is enhanced by the addition of nitric oxide synthase, nitric oxide synthase enhancers, nitric oxide donors, or other compounds that increase the nitrosation of the oocyte during fertilization. In another embodiment of the invention, the prevention of changes in nitric oxide levels in the oocyte, e.g. through the administration of NOS inhibitors, is used to block oocyte activation, where contraception is desired.

The present invention provides novel compositions and methods as set forth within this specification. In general, all technical and scientific terms used herein have the same meaning as commonly understood to one of ordinary skill in the art to which this invention belongs, unless clearly indicated otherwise. For clarification, listed below are definitions for certain terms used herein to describe the present invention. These definitions apply to the terms as they are used throughout this specification, unless otherwise clearly indicated.

Definition of Terms

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Oocyte. The term "oocyte," as used herein, means an oocyte which develops from an oogonium and, following meiosis, becomes a mature ovum. For example, an oocyte for purposes of the present invention may include metaphase II stage oocytes, matured either in vivo or in vitro. Mature metaphase II oocytes may be collected surgically from either non-superovulated or superovulated females, past the onset of estrus or past an injection of human chorionic gonadotrophin (hCG) or similar hormone. Alternatively, immature oocytes may be recovered from ovarian follicles and then matured in vitro by appropriate hormonal treatment and culturing.

Oocyte Activation: Activation of mammalian oocytes involves exit from meiosis and reentry into the mitotic cell cycle, and the formation and migration of pronuclei within the cell. Such a response in mammals is characterized by repetitive transient elevations in intracellular $Ca^{2+}$ levels followed by rapid return to base line.

Nitric Oxide Synthase: The enzyme nitric oxide synthase (NOS) catalyzes the formation of NO in multiple cell types. NOS isolated from different tissues show the existence of several isoforms, both constitutive and inducible forms, with specific cofactor requirements, mRNA sizes, and immunological properties. These may be calmodulin dependent or independent, and may use $BH_4$, FAD, FMN and/or $Ca^{2+}$ as cofactors. NOS present in spermatocytes is of interest, although other isoforms may be administered for use in the methods of the invention. A number of genetic sequences have been published for NOS proteins. For example, human endothelial NOSI may be accessed at Genbank no. D26607 (Miyahara et al. (1994) Eur. J. Biochem. 223 (3), 719–726); and an inducible NOS from heart muscle may be accessed at no. AF051164, (Adams et al. (1998) *Nitric Oxide* 2 (4), 242–249). It is highly probable that there is a specific isoform present in sperm. A truncated NOS has been identified in mouse and human sperm (Herrero et al. (1997) FEBS Lett. 411, 39–42); (Revelli et al. (1999). J. Cell. Physiol. 178, 85–92). Sperm often contain sperm-specific isoforms of proteins. Agents of interest may be targeted to gamete-specific isoforms of NOS.

The constitutive endothelial nitric oxide (NO) synthase (eNOS) can be activated by receptor-dependent and -independent agonists as a consequence of an increase in the intracellular concentration of free $Ca^{2+}$. Additional post-translational mechanisms regulate the activity of eNOS, including the interaction of eNOS with caveolin-1, heat shock protein 90 (Hsp90), or membrane phospholipids, as well as enzyme translocation and phosphorylation. Activation of eNOS can be induced by protein tyrosine phosphatase inhibitors.

Nitric oxide (NO) is synthesized from L-arginine by the NOS. The complex reaction involves the transfer of electrons from NADPH, via the flavins FAD and FMN in the carboxy-terminal reductase domain, to the heme in the amino-terminal oxygenase domain, where the substrate L-arginine is oxidized to L-citrulline and NO. The heme is essential for dimerisation as well as NO production.

Nitric Oxide Modulators: Modulators of nitric oxide fall into several categories. Of interest are inhibitors of NOS enzymatic activity; precursors of NO; inducers of the enzyme NOS or provision of the enzyme NOS itself; etc.

A number of NOS inhibitors have been described in the art. For example, substituted arginine derivatives are inhibitors. These include $N_G$-aminoarginine, $N_G$-nitroarginine, and $N_G$-alkyl arginines such as $N_G$-methylarginine, $N_G$-ethylarginine, $N_G$-propylarginine or $N_G$-butylarginine. Many substituents, for example, on the guanidino group of arginine or analogous citrulline or ornithine functional groups should function as well.

Mechanism-based in-activators are a class of NOS mechanistic inhibitors that require catalytic turnover to produce irreversible inactivation of the ability of NOS to generate NO. The inactivation process is associated with covalent modification of the NOS active site and proceeds either through heme destruction, its structural alteration, or covalent modification of the NOS protein chain, (see Bryk (1999) Pharmacol Ther Nov;84(2):157–78)

Other inhibitors include L-NAME; spiro-piperidine derivatives (U.S. Pat. No. 6,100,246, Hamley et al.); imidino piperidine derivatives (U.S. Pat. No. 6,071,906, Hansen et al.); pyrrolodino imidines (U.S. Pat. No. 6,043,261, Hansen et al.); 1,2,4-oxa diazolino and 1,24-oxa diazolidion heterocycles (U.S. Pat. No. 5,958,958, Hansen et al.); catechin derivatives, such as epigallocatechin-3-gallate or a related polyphenol (U.S. Pat. No. 5,922,756, Chan); etc.; as known and used in the art.

Agents that increase nitric oxide include sources for nitric oxide, such as S-nitrosopenicillamine, sodium nitroprusside, and nitric oxide gas itself.

The production of nitric oxide may be modulated by cytokines, such as γ-interferon, tumor necrosis factor, IL-1, IL-2 and endotoxin due to their effect on the enzyme, nitric oxide synthase. The inducible form of NO synthase is increased by cytokines and the constitutive form seems to be decreased by cytokines. The endothelial constitutive nitric oxide (NO) synthase (NOS III) can be activated by agonists as a consequence of an increase in the intracellular concentration of free $Ca^{2+}$ (Fleming (1997) J Vasc Res 34(3):165–74). The increase in $Ca^{2+}$ may be elicited by an increase in inositol 1,4,5-trisphosphate which is the consequence of tyrosine phosphorylation and activation of phospholipase C-gamma1 as well as protein tyrosine phosphatases. A pharmacologically identical activation of NOS III can be induced by protein phosphatase inhibitors.

HMG-CoA reductase inhibitors have been found to upregulate endothelial cell NOS activity, as described by U.S. Pat. No. 6,147,109, Liao et al.

NOS may be provided as the protein or an active fragment derived therefrom, or as a DNA construct for expression. DNA sequences may be employed for synthesis of the complete protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The sequence of the NOS polypeptide may be altered in various ways known in the art to generate targeted changes in sequence. The sequence changes may be substitutions, insertions or deletions, such as deletions of a domain or exon, providing for active peptide fragments of the protein. Other modifications of interest include epitope tagging, e.g. with the FLAG system, HA, etc. Such alterations may be used to alter properties of the protein, by affecting the stability, specificity, etc.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In some situations, it may be desirable to express the NOS gene in mammalian cells, where the protein will benefit from native folding and post-translational modifications.

The peptides may also be prepared by synthesis. Various commercial synthetic apparatuses are available, for example automated synthesizers by Applied Biosystems Inc., Foster City, Calif., Beckman, etc. By using synthesizers, naturally occurring amino acids may be substituted with unnatural amino acids, particularly diastereoisomers, side chains having different lengths or functionalities, and the like. The particular sequence and the manner of preparation will be determined by convenience, economics, purity required, and the like.

Methods of Use

Inhibition of NOS may be used as a contraceptive, to inhibit the activation of oocytes during fertilization. The inhibitors may be provided as a cream for vaginal delivery, as an extended release formulation, as a coating for condoms, and other topical or localized methods of administration, as known in the art. Such an inhibitor is preferably administered prior to fertilization, e.g. prior to intercourse as a contraceptive cream.

Methods for the enhancement of oocyte activation find particular use in combination with in vitro fertilization and other in vitro reproductive technologies, although in vivo uses are also contemplated. The oocytes may be activated in combination with fertilization, or may be activated in the absence of sperm. Activation is achieved by enhancing the nitric oxide levels of the oocyte. Methods for activation include providing NOS to the oocyte. While the cognate enzyme may be used, for example human sperm NOS in combination with human oocytes; it is not required. Any enzyme that has the appropriate enzymatic activity to produce NO can be used. The enzyme may be delivered as the protein, or as a DNA expression vector encoding the protein; mRNA encoding the protein, and the like.

The natural activity of sperm may be enhanced by the administration of NO sources, such as S-nitrosopenicillamine; enhancers of NOS expression, and the like.

For in vitro fertilization the agents are administered in a suitable culture medium appropriate for the maintenance and activation of oocytes. For in vivo administration the agents may be formulated in a pharmacologically acceptable carrier.

The action of NO is mediated through cyclic GMP, and so compounds that interfere with cGMP metabolism may also find use as effective fertility enhancers or inhibitors. For example, Viagra acts by inhibiting the degradation of cGMP which is produced by NO stimulation of NOS during penile erection. Specific inhibitors or enhancers of cGMP metabolism in the oocyte may affect the activation of the oocytes.

The method of the invention find use in a wide variety of animal species, including invertebrate species such as sea urchins; birds, mammalian species, etc. Animal models, particularly small mammals, e.g. murine, lagomorpha, etc. are of interest for experimental investigations. Animal models, particularly small mammals, e.g. murine, lagomorpha, etc. are of interest for experimental investigations. Other animal species may benefit from improvements in in vitro fertilization, e.g. horses, cattle, rare zoo animals such as panda bears, large cats, etc. Humans are of particular interest for both enhancing oocyte activation, and for methods of contraception.

The pharmacologically active agents employed in the methods of the present invention may be administered in a mixture with conventional excipients, i.e., pharmaceutically acceptable liquid, semi-liquid or solid organic or inorganic carriers suitable, e.g., for parenteral or enteral application. Suitable pharmaceutically acceptable carriers include but are not limited to: water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythriotol fatty acid esters, hydroxymethylcellulose polyvinyl pyrrolidone, and the like. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

Particularly suitable for parenteral application are oily or aqueous solutions, suspensions, emulsions, implants, intrauterine devices and suppositories. Ampoules offer convenient unit dosages.

For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coating, etc.

The agents or combination can be administered as a mixture with any other optional active agent or as a separate unit dosage form, either simultaneously or at different times during the day from each other.

EXPERIMENTAL

Example 1

The present data demonstrates that nitric oxide (NOS) is present and active in gametes. Immunoblot analysis of sperm homogenates with a polyclonal antibody specific for the highly conserved calmodulin (CaM)-binding domain of rat neuronal NOS (nNOS) reveals a single immunoreactive band of approximate relative molecular mass 140,000 (Mr 140K). Pre-incubation of the anti-nNOS antibody with its peptide antigen blocks immunoprecipitation of the 140K protein, whereas immunoprecipitation with protein G-agarose alone does not precipitate the 140K protein. When homogenates are probed with a monoclonal 'universal' NOS (uNOS) antibody, recognizing domains conserved among the inducible, endothelial and neuronal NOS isoforms, a distinct band of Mr 140K is again observed. Densitometric analysis shows that the sperm NOS isoform is present at high concentration ($0.44 \pm 0.05\%$ of total NP-40 soluble sperm protein; n=4). An immunoreactive band of Mr 175K is also present in eggs, as shown by the anti-uNOS antibody or anti-nNOS antibody.

Immunolabelling intact sperm with the anti-nNOS antibody prominently stains the head, acrosomal region and midpiece, with minor staining of the tail. Midpiece staining is also seen with nonspecific IgG, whereas staining of the sperm head and particularly a punctate 'dot' at the anterior, acrosomal end of the sperm is only observed with anti-nNOS antibody, indicating that NOS is concentrated in these regions and consistent with sperm-borne delivery of NOS after sperm-egg fusion.

Figure 1A:
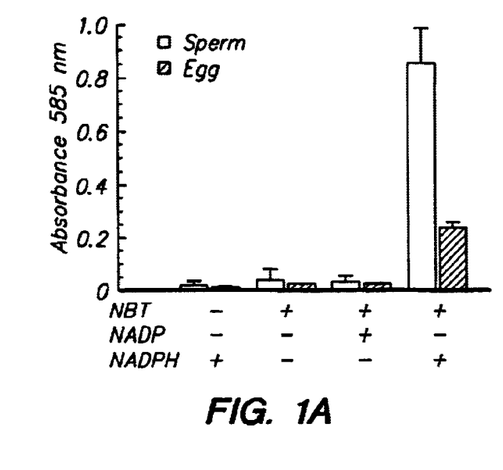
FIG. 1A shows diaphorase activity of gamete homogenates in the presence or absence of NBT, NADP or NADPH as indicated. Absorbance at 585 nm was measured and normalized to total protein.
Figure 1B:
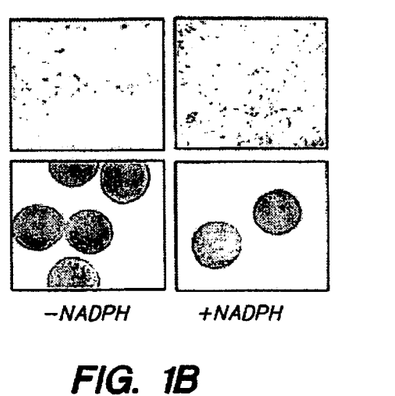
FIG. 1B shows NADPH diaphorase staining of gametes in the presence or absence of NADPH. This diaphorase activity is indicative of NOS activity.
Figure 1C:
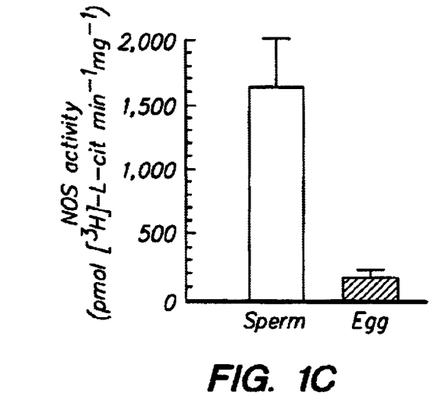
FIG. 1C shows $^3$H arginine to $^3$H citrulline conversion in gamete homogenates.
Figure 1D:
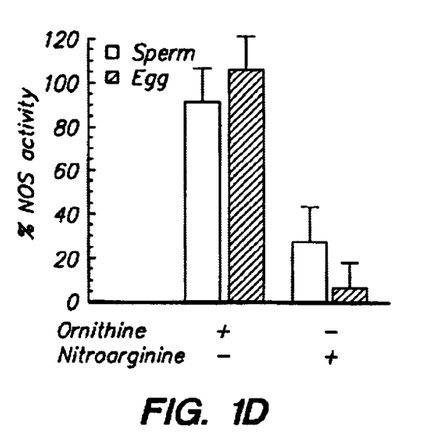
FIG. 1D shows the activity (relative to controls) in the presence of ornithine (1.5 mM) which inhibits non-NOS citrulline conversion or $N^6$-nitro-L-arginine (100 μM) which inhibits NOS-mediated conversion of citrulline.
Figure 1E:
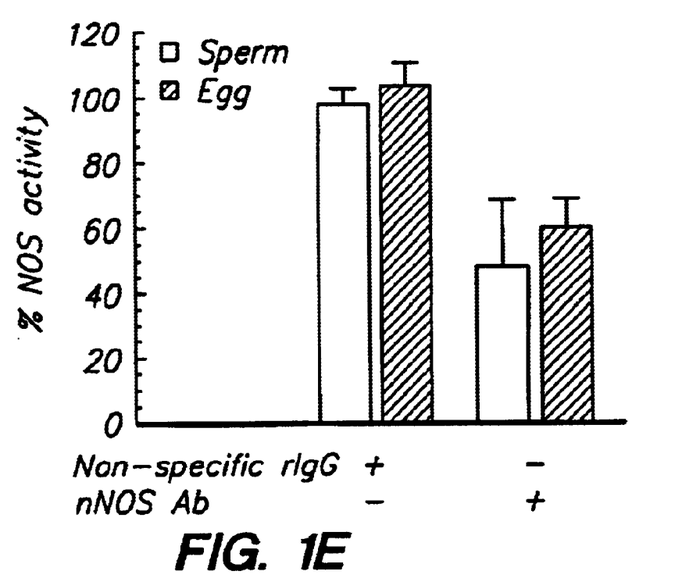
FIG. 1E shows the immunodepletion of NOS activity from gamete homogenates. NOS activity is shown measured by citrulline conversion.
Figure 1F:
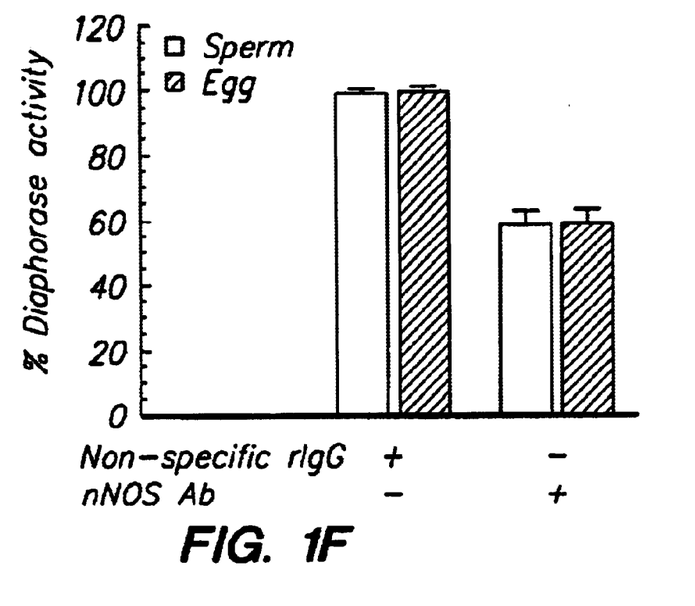
FIG. 1F shows NADPH-dependent diaphorase activity after depletion with anti-nNOS antibody.

NOS is enzymatically active in both gametes, as determined by NADPH (nicotinamide-adenine dinucleotide phosphate)-dependent diaphorase activity4 measured spectrophotometrically or by whole-cell diaphorase staining (FIG. 1A) and by the more specific citrulline assay (FIG. 1B). Diaphorase staining is apparent in the head and tail regions of sperm and evenly distributed throughout the entirety of eggs (FIG. 1B). The citrulline conversion exhibited by gametes might result from urea cycling; however, there is no inhibition with ornithine, a urea cycle inhibitor, whereas NG-nitro-L-arginine, a specific NOS inhibitor, greatly suppresses citrulline conversion activity (FIG. 1C). The citrulline conversion and diaphorase activity is depleted by NOS immunoprecipitation from gamete homogenates, further showing the specificity of the anti-nNOS antibody (FIG. 1E).

We measure production of NO by gametes by accumulation of nitrite, an auto-oxidation product of NO, or by fluorescence changes in the NO indicator dye, diaminofluorescein (DAF). Qualitatively similar results are seen for exogenous NO production: activation of either male or female gametes results in NO accumulation in the surrounding medium (Table 1). For sperm, egg jelly is more effective than ionomycin in eliciting NO increases that are nonlinear with increasing sperm concentration, possibly because of auto-inhibition of NOS by NO. Inhibition of sperm motility does not affect NO production. Pre-treatment with inhibitors of the acrosome reaction, substantially prevents NO generation, but is triggered after subsequent addition of ionomycin (Table 2). Similarly, eggs activated by ionomycin treatment generate NO, although at lower levels than sperm (Table 1).

TABLE 1

NO production after gamete activation

| Gamete | Treatment | Nitrite (pmol) | DAF Fluorescence (arbitrary units) |
|---|---|---|---|
| Sperm (1 µl) | SW, pH 8 | 23 ± 10 | 22 ± 3 |
|  | Ionomycin | 75 ± 30 | 103 ± 13 |
|  | EJ | 310 ± 15 | 170 ± 49 |
| Sperm (5 ml) | SW, pH 8 | 75 ± 15 | 42 ± 6 |
|  | ionomycin | 153 ± 15 | 543 ± 35 |
|  | Egg jelly | 465 ± 15 | 1,108 ± 108 |
| Sperm (10 ml) | SW, pH 8 | 138 ± 15 | 70 ± 14 |
|  | Ionomycin | 283 ± 15 | 910 ± 93 |
|  | Egg jelly | 610 ± 15 | 1,423 ± 169 |
| Eggs (1%, v/v) | SW, pH 8 | 25 ± 5 | 25 ± 5 |
|  | Ionomycin | 64 ± 4 | 56 ± 10 |
| Eggs (2%, v/v) | SW, pH 8 | 30 ± 7 | 28 ± 4 |
|  | Ionomycin | 82 ± 9 | 76 ± 8 |
| Eggs (5%, v/v) | SW, pH 8 | 33 ± 8 | 37 ± 5 |
|  | Ionomycin | 141 ± 10 | 112 ± 6 |

NO production in *S. purpuratus gametes* was determined by measuring nitrite accumulation or DAF fluorescence. Sperm (1, 5 or 10 ml) were incubated in seawater (SW, pH 8), 5 mM inomycin, or egg jelly for 5 min and exogenous NO was measured. Similarly, eggs (1%, 2% or 5% suspension) were incubated in SW or 1 mM ionomycin for 5 min and exogenous NO was measured. Ionomycin and egg jelly values were normalized to per cent acrosome reaction after subtraction of background fluorescence.
Total nitrite was determined by converting fluorescence values using nitrite standard curves. Data are from at least four experiments.

TABLE 2

Sperm NO production is dependent on acrosome reaction

| Treatment | DAF Fluorescence (%) |
|---|---|
| Egg jelly | 100.0 ± 0.0 |
| Verapamil | 37.8 ± 4.0 |
| WGA | 6.4 ± 1.2 |
| (Egg jelly + verapamil) + ionomycin | 75.7 ± 9.7 |
| (Egg jelly + WGA) + ionomycin | 58.3 ± 6.1 |

Packed sperm (5 µl) were incubated in the presence or absence of the acrosome reaction inhibitors verapamil (100 µM) or wheat germ agglutinin (WGA; 50 µg ml) for 10 min and NO was measured after addition of egg jelly or egg jelly with 5 µM ionomycin, as indicated. Under these conditions, less than 3% of sperm were acrosome-reacted as compared with 85% for controls. Data are from three separate experiments.

Figure 2A:
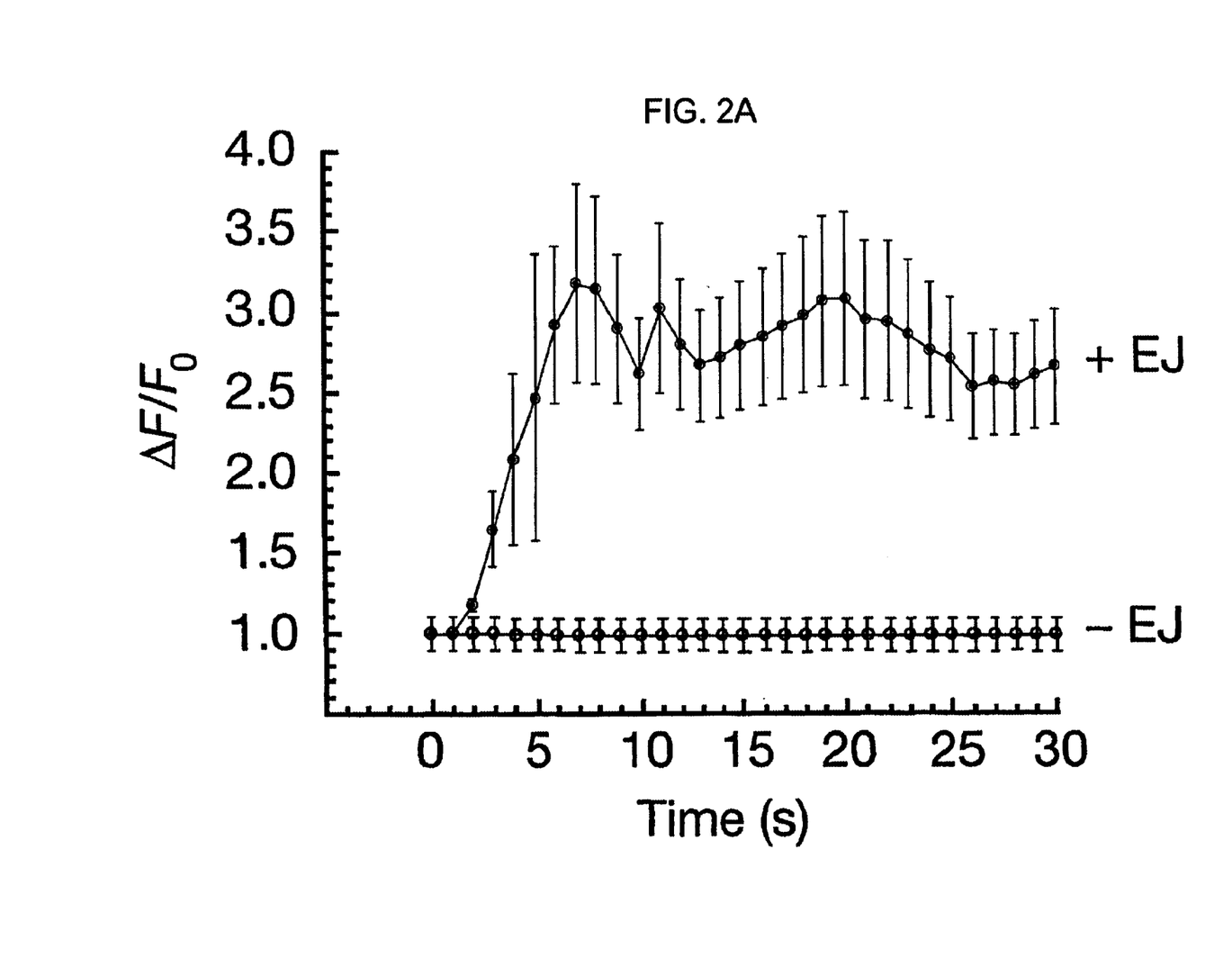
FIG. 2A shows the $\Delta F/F_o$ intensity for egg-jelly-stimulated sperm or seawater-treated sperm.
Figure 2B:
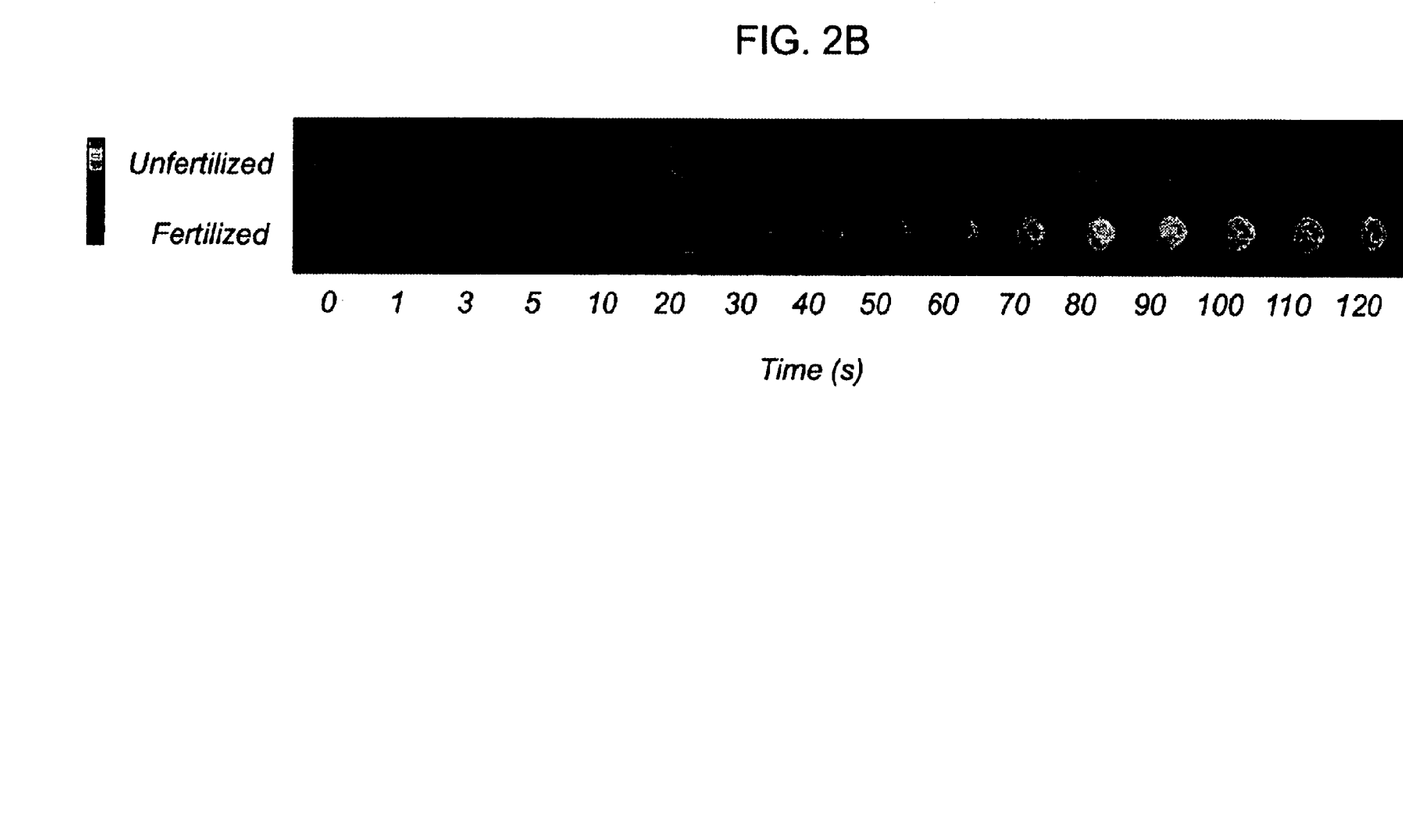
FIG. 2B shows the nitrosation in eggs in fertilization, with representative images at 0, 1, 3, 5 and 10 s intervals for unfertilized and fertilized eggs (1:10,000 sperm dilution added at time t=0).
Figure 2C:
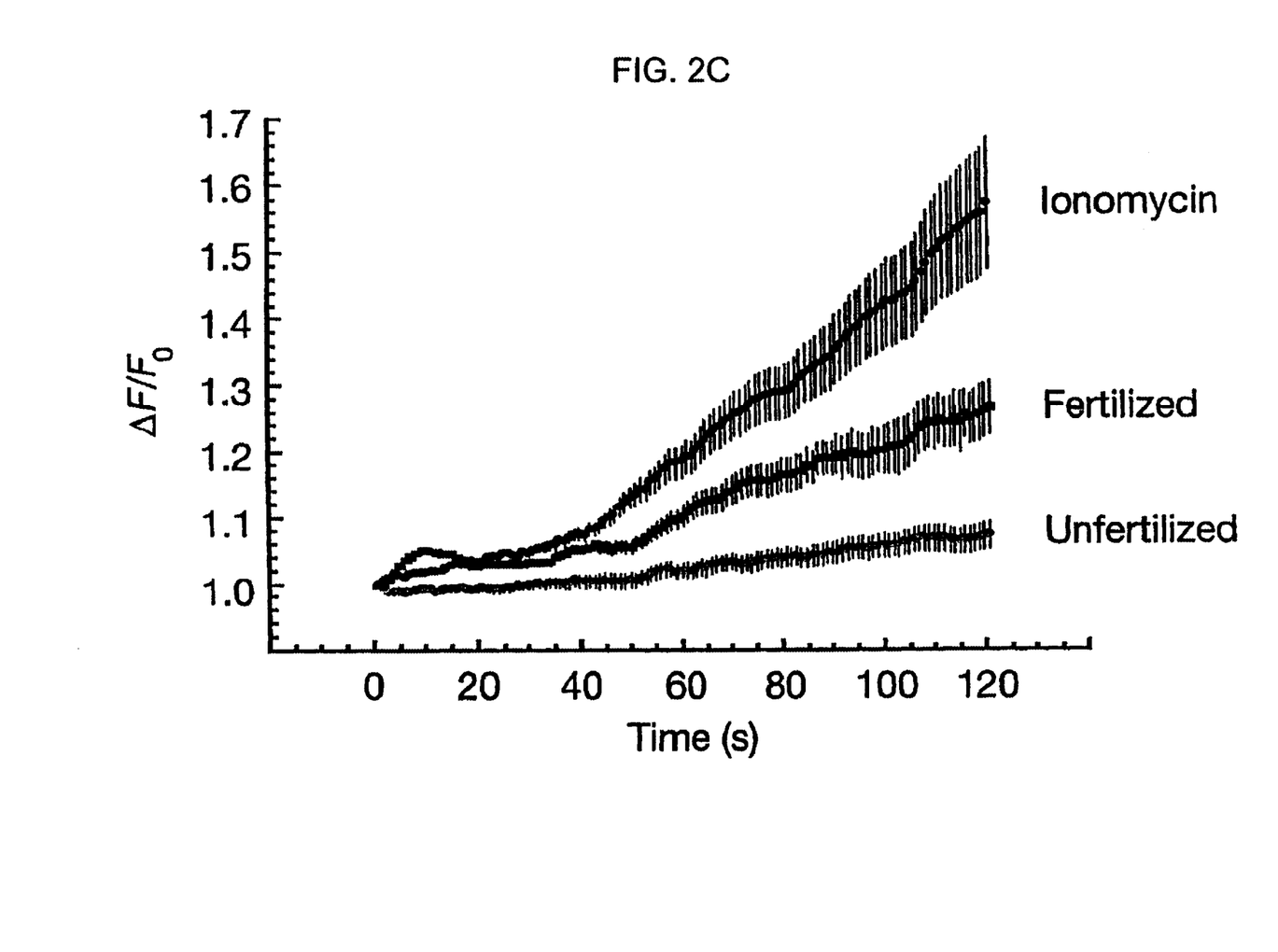
FIG. 2C shows $\Delta F/F_o$ intensity (over entire egg) for unfertilized eggs, fertilized eggs and ionomycin-treated eggs (2 μM). Results are mean ±s.d. and significant (P<0.01 Student's t-test, n=5 and 34) for fertilized eggs.

A cell-permeable, diacetate form of DAF allows real-time, in vivo visualization of NO within sperm during the acrosome reaction (FIG. 2A), and eggs at fertilization (FIG. 2B). After egg-jelly-elicited activation, NO rapidly increases in sperm (FIG. 2A), primarily in the head region, with a timing similar to the acrosome reaction (FIG. 2A). Similarly, NO changes occur in eggs at fertilization: an initial transient between 0 and 5 s is followed 30–35 s later by a more gradual, sustained increase over minutes (FIG. 2b). Prior injection of oxyhemoglobin (oxyHb), a physiological scavenger of NO, largely eliminates NO increases in DAF fluorescence (77.3±10.4% inhibition; 8 injected eggs). These findings are consistent with work showing early increases in cGMP and cADPR, both of which are NO dependent.

Figure 3A:
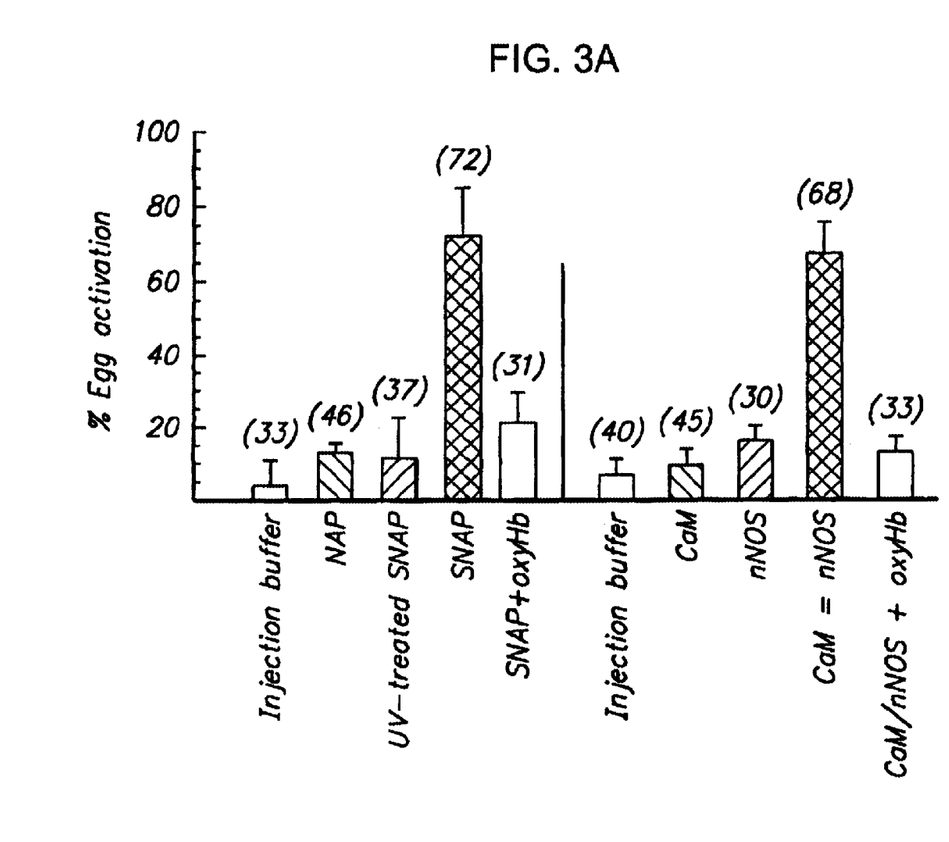
FIG. 3A depicts injection of the NO donor SNAP, NAP, ultraviolet treated SNAP (5 μM final concentration) or recombinant nNOS (0.0075 pg final) with CaM (0.125 pg final) or either alone. Also, co-injection of SNAP or CaM/nNOS with oxyHb.

Mimicking the NO increase by increasing intracellular NO leads to egg activation. Eggs injected with the NO donor S-nitrosoacetylpenicillamine (SNAP) or recombinant nNOS with calmodulin (CaM) activate in terms of fertilization-envelope elevation (a calcium-dependent exocytotic event) (FIG. 3a) and pronuclear centering (13 out of 13 eggs exhibiting a full fertilization envelope). Bath application of NO is ineffective. SNAP and nNOS are only effective over a narrow concentration range; levels above the activating concentration are ineffective, and eggs exposed to high NO concentrations are in fact refractory to activation by sperm. Activation by SNAP is dependent on the presence of the releasable NO group; N-acetylpenicillamine (the non-S-nitrosylated starting material for SNAP synthesis) and light-decomposed SNAP are ineffective in activating eggs (FIG. 3A). Similarly, activation of eggs by the $Ca^{2+}$/CaM dependent nNOS isoform requires CaM; CaM alone or nNOS alone are insufficient (FIG. 3A). Egg activation does not occur when SNAP or CaM/nNOS are co-injected with oxyHb (FIG. 3A).

Figure 3B:
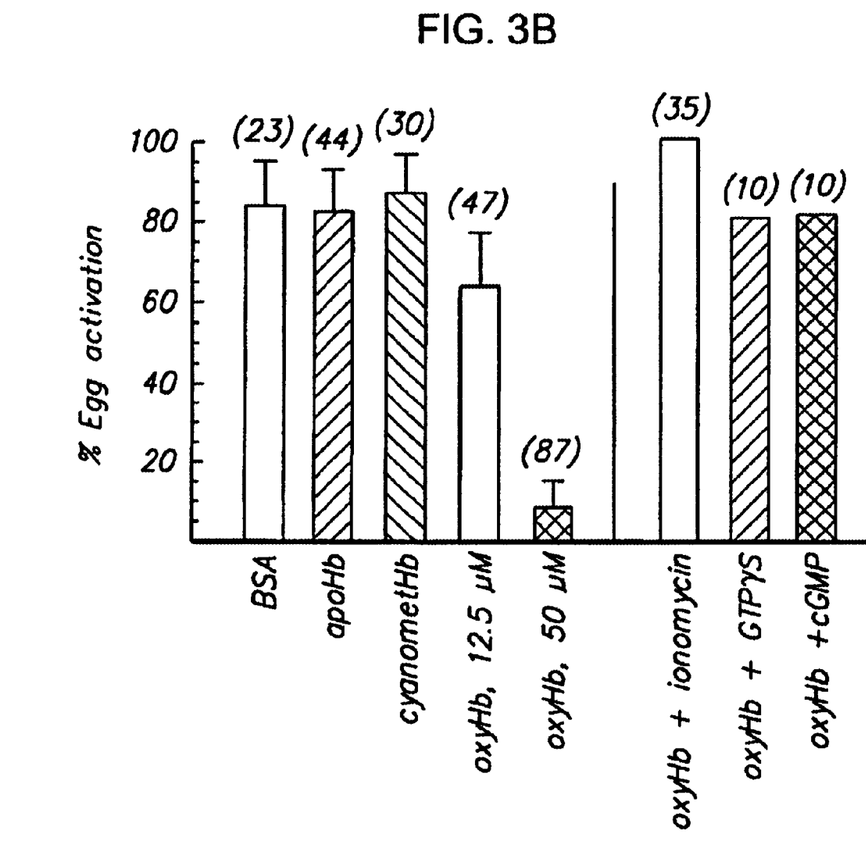
FIG. 3B shows eggs injected with oxyHb (12.5 μM or 50 μM protein final) or 50 μM BSA, apoHb or cyanometHb and inseminated (1:20,000 sperm dilution). Subsequent activation of oxyHb-inhibited eggs by ionomycin (2 μM) or injection of either GTP$_\gamma$S (100 μM final) or cGMP (50 μM final). The number of eggs is listed in parentheses.
Figure 3C:
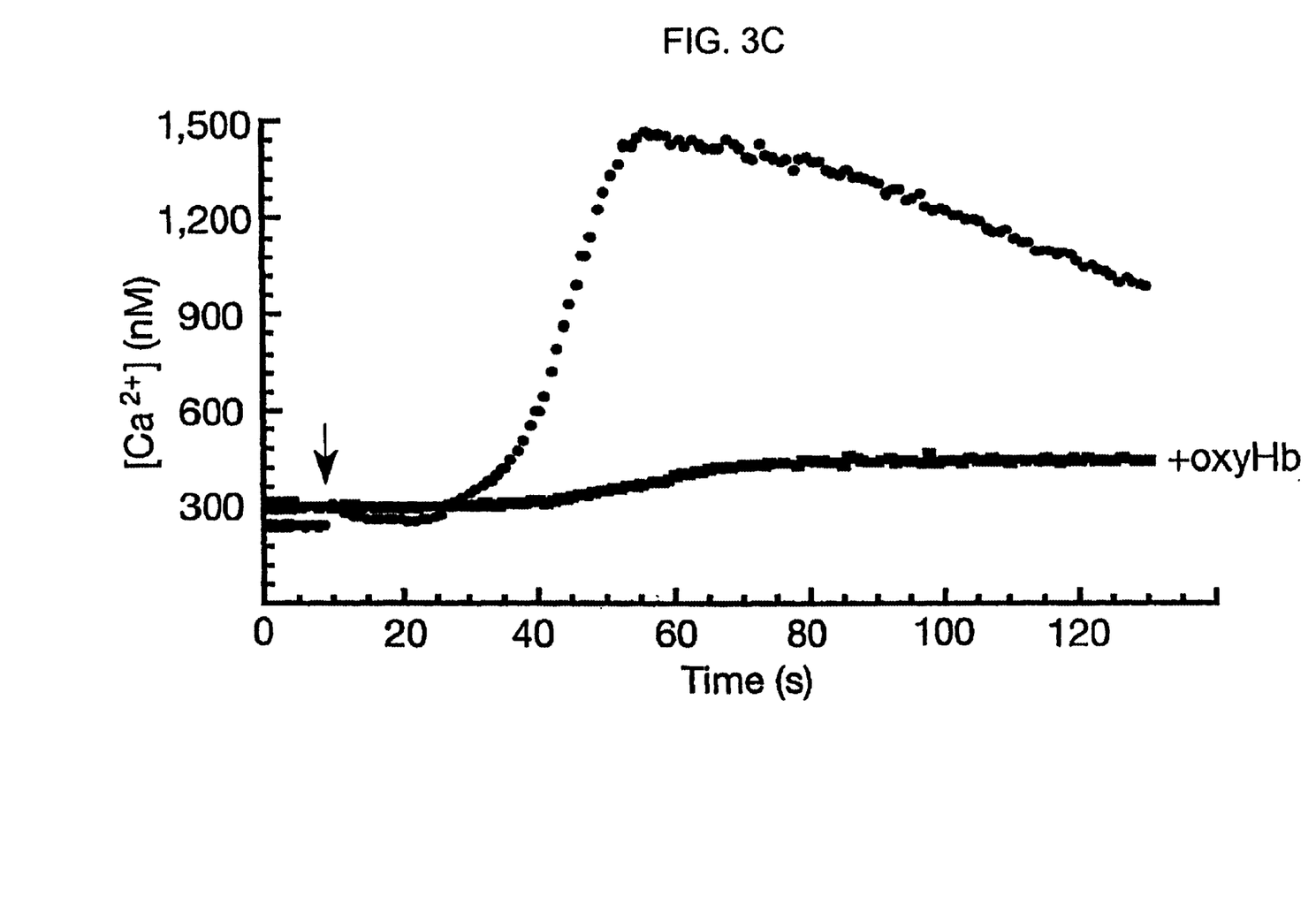
FIG. 3C shows representative trace of calcium release in the presence or absence of oxyHb measured by calcium green-2. Arrow indicates the time of sperm-egg fusion.

The necessity of NO (or its equivalents) was assessed by injecting eggs with oxyHb. Fertilization envelope elevation is dose-dependently inhibited in oxyHb-injected eggs (FIG. 3B) and other calcium-dependent indicators of egg activation, pronuclear centering and first cell division, are also lacking (0 out of 15 eggs). OxyHb-inhibited eggs can, however, elevate fertilization envelopes after insemination if subsequently treated with ionomycin or microinjected with GTPS or cGMP, showing that calcium stores, and more specifically the inositol trisphosphate ($IP_3$) and cGMP calcium-releasing pathways, are intact and operative in the presence of oxyHb. Inhibition of calcium mobilization is specific for scavenging of NO-related bioactivity by oxyHb as egg activation is not significantly affected in eggs injected with either bovine serum albumin (a nitrosylable protein), apoHb (Hb lacking the heme moiety) or cyanometHb (Hb functionally blocked at the heme moiety) (FIG. 3b). Accordingly, the calcium rise is substantially reduced in oxyHb-injected eggs (240±30 nM resting $Ca^{2+}$ to 1.4±0.2 µM peak $Ca^{2+}$ post-fertilization compared with 280±65 nM resting $Ca^{2+}$ to 540±95 nM peak $Ca^{2+}$ in oxyHb-injected eggs; 15 control and 14 oxyHb-injected eggs with n=2), indicating that sperm enter these eggs, but fail to generate a calcium rise sufficient to elicit egg activation (FIG. 3c).

The nature of the NO-related bioactivity suggests potential mechanisms connecting sperm-egg fusion to initiation of the calcium rise at fertilization. In eggs, exogenously applied NO increases cGMP and cADPR (cyclic ADP-ribose) and elicits calcium release from ryanodine receptor (RyR)-gated stores, but the ensuing calcium level does not result in activation. Similarly, despite early increases in cGMP and cADPR at fertilization, this pathway is apparently not required. Unlike exogenous NO, endogenous NO (or its equivalents) is sufficient for egg activation, suggesting that there are signaling pathways in addition to cGMP/cADPR that are only accessible intracellularly. One such pathway may be the direct release of calcium by S-nitrosylation of RyR stores which may induce additional calcium release by stimulating a calcium-sensitive phospholipase C and resultant $IP_3$ production. In addition, like phosphorylation, nitrosylation can trigger signaling intermediates such as src which in turn may elicit phospholipase C activity. The pleiotropic signaling provided by NO through cGMP/cADPR formation and S-nitrosylation could account for the diverse modes of calcium release seen at fertilization, and, consequently, NO may be an universal activator of eggs or oocytes.

Methods

Materials. Gametes (*S. purpuratus* and *L. pictus*) were collected as described, and concentrated egg jelly was prepared by acid-washing eggs. For nitrite determinations, egg jelly was prepared in an artificial seawater (nASW) with reduced divalent cations comprising (in mM): 519 NaCl, 5 $MgCl_2$, 5 CaCl 2, 2 $NaHCO_3$, 10 KCl and 10 glycylglycine, pH 8. DAF was from Daiichi Pure Chemicals and recombinant nNOS and CaM were from Stratagene.

Immunoblotting and Immunolabelling. Coelomocyte-free sperm or washed, de-jellied eggs were lysed in ice-cold buffer (1% NP-40 in 150 mM NaCl, 50 mM Tris, pH 8) with a protease inhibitor cocktail (PIC: bestatin, pepstatin, aprotinin, leupeptin, AEBSF, E-64 and SBTI), pelleted, and the supernatants boiled immediately before separation by SDS-poly acrylamide gel electrophoresis and immunoblotting. Egg homogenates required immunoprecipitation before immunoblotting with anti-nNOS antibody. Polyclonal anti-nNOS antibody (1:2,000) raised against the peptide sequence (SEQ ID NO:1) [$T_{724}$KRRAIGFKKLAEAVK$_{739}$C] corresponding to the CaM-binding domain of rat nNOS (Affinity Bioreagents), or mouse ascites anti-uNOS (1:5) raised against conserved domains of iNOS, eNOS and nNOS were used. Anti-nNOS was used at 1:200 dilution for immunoprecipitation. Anti-nNOS peptide antigen was provided by Affinity Bioreagents. Image Pro 4.0 was used for densitometry with recombinant nNOS for comparison. Protein was quantitated by the Bradford protein microassay (BioRad) using BSA as a standard. Anti-nNOS (1:50) and Cy2-conjugated secondary antibody (1:50) were used for NOS immunolabelling with 0.1% Triton X-100, 1% PVP-40, 2% BSA and 5% goat serum in PBS for the blocking and washing steps.

NO/NOS assays. NADPH-dependent diaphorase activity or histochemical staining was assessed after a 24-h fixation of gametes. For activity measurements, gametes were lysed (sperm) or sonicated (eggs) in PBS with 1% NP-40 and incubated overnight in 1 mM NADPH, 0.5 mM NBT. Immunodepletion of diaphorase activity was done after size separation (>100K molecular weight cut-off (Amicon)). [$^3$H]arginine to [$^3$H]citrulline conversion of gamete homogenates was assessed after two cycles of freeze-thaw lysis (sperm) or Dounce homogenization (eggs) (in mM): 50 KCl, 10 NaCl, 1 EDTA, 5 DTT, 20 HEPES with PIC; pH 8. For inhibition experiments, gamete homogenates were treated with 20% (v/v) activated Dowex to remove endogenous arginine. Nitrite determinations were performed using nASW to avoid divalent cation precipitation by the stop buffer (0.5 M EDTA in 6.7 N NaOH). nASW did not affect the percentage of spontaneous or elicited acrosome reaction as judged by the 'thumb squash' method. NO determination by DAF fluorescence (490/515 nm) was done after incubating gametes in seawater containing 10 $\mu$M DAF.

NO and $Ca^{2+}$ Imaging. Eggs were loaded in 10 $\mu$M DAF-DA in seawater, pH 8 (30 min at 15° C.). Sperm were loaded similarly in calcium-free artificial seawater (pH 6), but we observed a light-dependent increase in DAF fluorescence caused by nitrosylation of endogenous thiols during loading and subsequent photolytic release of NO. This was eliminated by including 150 $\mu$M carboxy-PTIO (a cell-impermeant NO scavenger) and 0.1 mM EDTA during incubation. After loading, eggs or sperm were washed thoroughly and transferred to a temperature-controlled chamber (20° C.) on a Nikon Diaphot microscope equipped with a SIT camera. Eggs were imaged with a 20 Fluor (N.A.=0.75) objective and sperm with a 100 (N.A.=1.4) objective. ImagePro 4.0 was used for data analysis and pseudocolouring. Calcium measurements were done using calcium green-2 and calibrated using 1% Triton X-100 to determine Fmax/Fmin.

Microinjection. L. pictus eggs were injected to 2% egg volume using intracellular injection media comprising (in mM): 250 glycine, 250 K$^+$-gluconate, 10 HEPES, 10% PVP-40 (w/v), pH 7.0 (adjusted with acetic acid) and eggs were attached to surfaces with 10 mg ml$^{-1}$ protamine sulfate. SNAP and oxyHb were loaded at 4° C. in the dark and injections were performed using a red filter to prevent auto-oxidation of the oxyHb or photolysis of the SNAP. Dialyzed, chromatographically pure oxyHb, apoHb and cyanometHb were prepared and concentrated at 4° C. in injection media supplemented with 0.1 mM EDTA and allowed to equilibrate for 30–45 min before insemination. The fully oxygenated status and concentration of oxyHb were determined by Soret absorbance at 415 nm. SNAP was synthesized before use. For control experiments, SNAP was decomposed by a 5-min mercury lamp exposure. Recombinant CaM-nNOS complexes were formed by mixing the stock CaM solution at a 1:1 ratio with the appropriate nNOS dilution in injection media and kept on ice before use. Egg batches that exhibited greater than 10% spontaneous activation or less than 80–85% activation after insemination were discarded. Control and experimental injections were done within the same batch of eggs.

Nitrite accumulation as measured by DAN fluorescence is not suitable for continuous in vivo measurement of NO production due to the harsh assay conditions. Diaminofluorescein (DAF), offers a number of advantages over DAN or other methods of monitoring NO. First, the fluorescein-based structure should be non-toxic. Second, the diacetate and membrane-permeant form of DAF (DAF-DA) allows visualization of in vivo nitric oxide within sperm and eggs without the necessity of microinjection. Third, the dye is highly sensitive (~5 nM) and specific for NO (or its equivalents). In addition, DAF should not interfere with NO signaling as it interacts with an intermediate oxidized form of NO. It is important to note that DAF forms a stable covalent fluorescent product whereas traditional reporter dyes such as fura-2 form dissociable complexes. The absolute DAF fluorescence at any time reflects the integral of nitric oxide to that point and the dynamics of nitric oxide changes are measured by the first derivative of fluorescence changes rather than the absolute fluorescence at each time point.

Because DAF is a relatively new dye, we did additional control experiments to ensure that fluorescence increases were specific for NO (or its equivalents) and not other unrelated, physiological increases which occur at fertilization (e.g. pH or calcium). We found that DAF fluorescence did not increase when the NO auto-oxidation products $NO_2$ and $NO_3$ or the oxidant $H_2O_2$ were added (Table 3). Other potential oxidants such as ONOO$^-$ do not react with DAF and fluorescence increases are linear with increasing concentrations of NO donor. Calcium itself or increased pH does not cause increased DAF fluorescence. The NO donor SNAP gave dose-dependent increases in DAF fluorescence which were inhibitable by the NO scavenger, carboxy-PTIO. Similarly, arginine analogs which inhibit NOS activity suppress DAF fluorescence increases in stimulated bovine aortic endothelial cells and NIE-115 neuroblastoma cells. Together, these data demonstrate that DAF is specific for NO (or its equivalents) and fluorescence increases require the presence of NO.

TABLE 3

$NO_2$, $NO_3$, $H_2O_2$, pH and $Ca^{2+}$-sensitivity of DAF

| Condition | DAF Fluorescence (Arbitrary units) |
|---|---|
| control | 18.0 ± 0.8 |
| +10 $\mu$M $NO_2$ | 17.5 ± 0.5 |
| +10 $\mu$M $NO_3$ | 17.5 ± 0.5 |
| +100 $\mu$M $H_2O_2$ | 18.5 ± 0.7 |
| control | 13.2 ± 0.5 |

TABLE 3-continued

NO$_2$, NO$_3$, H$_2$O$_2$, pH and Ca$^{2+}$-sensitivity of DAF

| Condition | DAF Fluorescence (Arbitrary units) |
|---|---|
| +10 µM CaCl$_2$ | 13.2 ± 0.5 |
| pH 6.5 | 27.4 ± 0.5 |
| pH 7.0 | 23.7 ± 0.6 |
| pH 7.5 | 21.0 ± 1.0 |
| pH 8.0 | 19.4 ± 0.5 |

Specificity of Diaminofluorescein (DAF). NO$_2$, NO$_3$, H$_2$O$_2$, Ca$^{2+}$, and pH sensitivity of DAF fluorescence. DAF (10 µM) fluorescence measured in the absence or presence of the indicated ion. Fluorescence measurements were done in SW, pH 8 for NO$_2$, NO$_3$, and H$_2$O$_2$ whereas double distilled water was used in the Ca$^{2+}$ determinations. Similarly, SW at the indicated pH was used in the fluorescence measurements examining pH sensitivity. All measurements were done at room temperature.

NO/NOS Calculations The amount of NOS or SNAP injected to effect activation is similar to that contained or produced by a single spermatozoon. From Table I, 1 µL of sperm produces ~310 pmol of NO. Assuming 1 µL of packed sperm represents ~4×10$^7$ spermatozoa$^5$, an individual spermatozoon generates ~7.75 attomoles of NO. This amount is likely an underestimation of actual NO production given the reactivity of NO and the number of un-assayable side reactions. However, using these assumptions, it follows that even distribution would result in a NO concentration of ~30 nM across the egg (assuming a diameter of 80 µm). NO action would be localized initially and taking an arbitrary hemispheric region of 5 µm as the site of sperm-egg fusion, the NO concentration here would be ~7.2 µM. Similarly, we expect approximately 0.0044 pg of NOS/spermatozoon or equivalently 0.005 pg of recombinant nNOS/spermatozoon (assuming 1 pg total protein/spermatozoon). Actual injected SNAP yielding activation was ~5 µM final and nNOS was ~0.0075 pg.

Example 2

Activation of Mammalian Oocytes

Bovine oocytes were ordered from Bomed (2433 University Avenue, Madison, Wis. 53705-3835). They collect the oocytes from the ovaries of slaughtered cows and place them immediately in maturation media to be shipped overnight. Oocytes were matured overnight and used within 24–28 hours of collection. Oocytes were washed briefly three times in TL-HEPES media and then denuded by vortexing for 3 minutes in TL-HEPES containing 0.2% hyaluronidase. Denuded oocytes were subsequently washed in TL-HEPES and loaded with fura-2 AM by incubation at 37° C. for 15 to 30 minutes. Oocytes were attached to imaging dishes (Biopteks) using 50 µg/ml poly-D-lysine and imaged using 350/380 nm excitation and 510 nm emission filters on a Zeiss Axiovert S100 microscope and fluorescence intensity quantified using Metafluor 4.1 (Universal Imaging).

Figure 4:
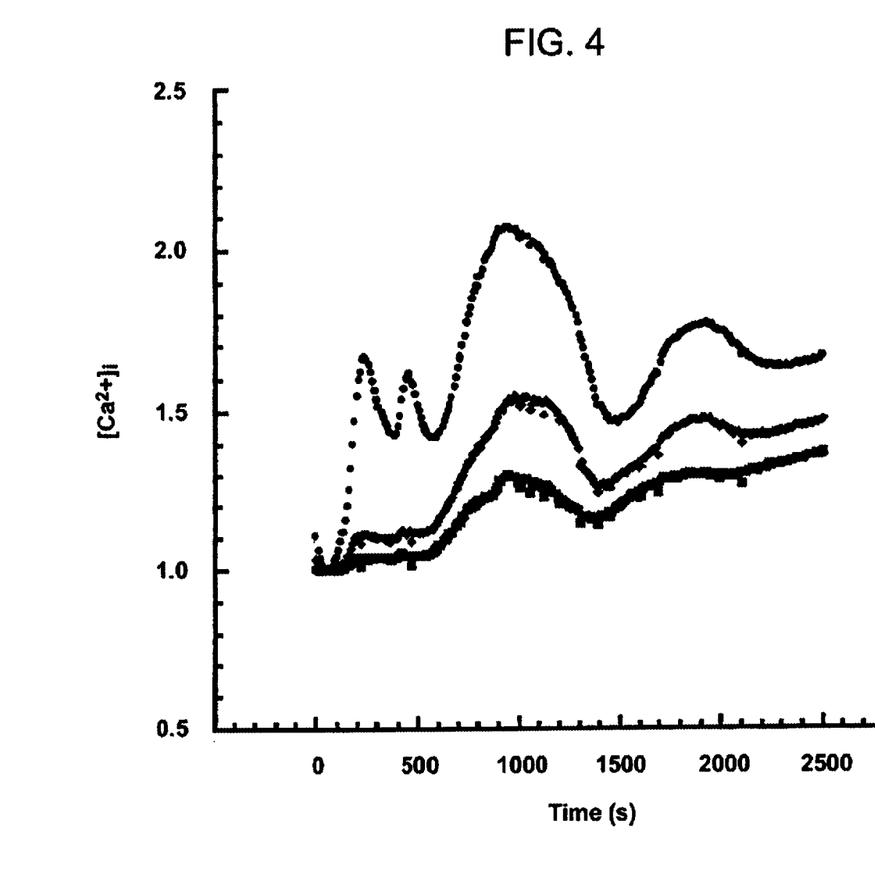
FIG. 4 shows that SNAP (a NO donor) can cause calcium oscillations in bovine oocytes.

FIG. 4 shows the calcium oscillations induced by NO. This is important because mammalian oocytes are believed to require calcium oscillations rather than a single calcium wave (which occurs in sea urchin eggs). SNAP (S-nitrosopenicillamine), an NO donor was synthesized prior to use by the method of Fehsel et al. (1996) *Meth. Enzymol.* 269:426–434. NO release was accomplished by bath addition of SNAP. Calcium release could be effectuated by addition of SNAP at varying concentrations (0.5 mM to 5 mM).

Figure 5:
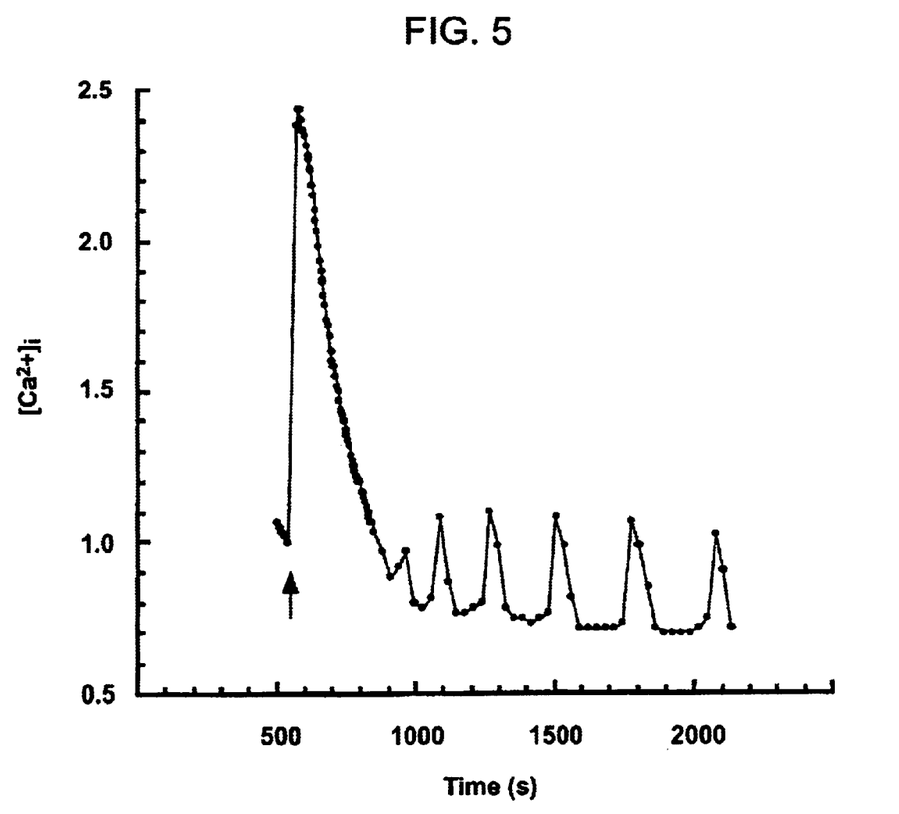
FIG. 5 shows calcium oscillations in bovine oocytes following injection of an extract from porcine sperm.
Figure 6:
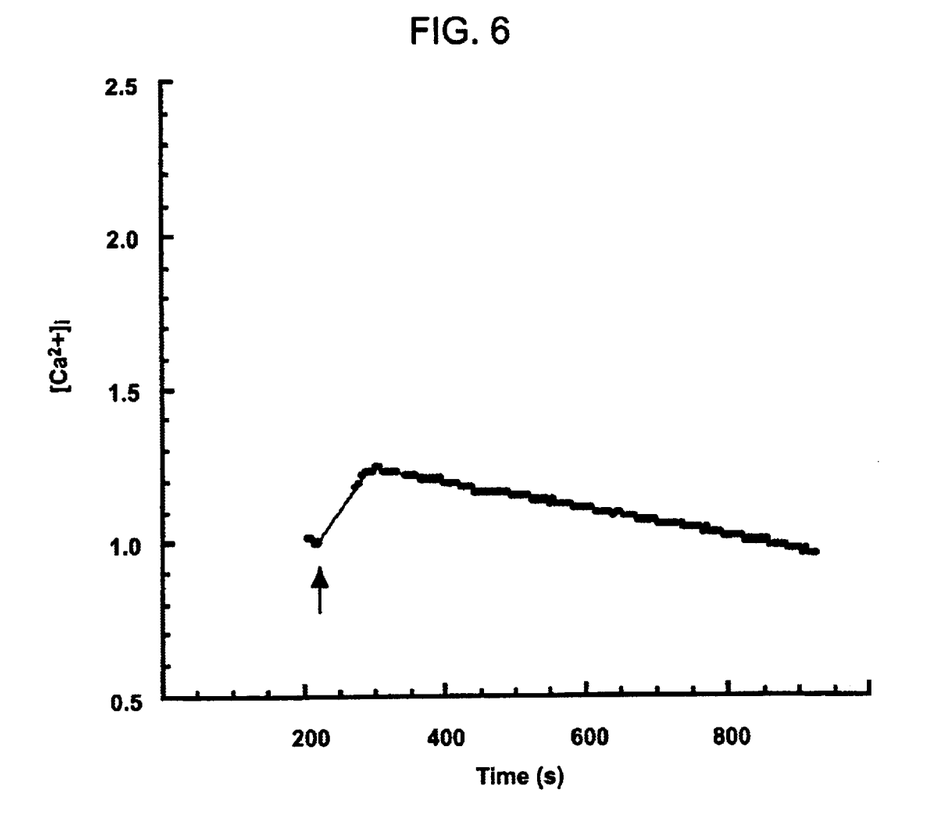
FIG. 6 shows inhibition of calcium oscillations in bovine oocytes following injection of the same porcine sperm extract when oxyHb (a NO scavenger) is pre-injected into bovine oocytes.

FIGS. 5 and 6 show inhibition of sperm factor induced calcium oscillations by oxyhemoglobin. Sperm factor was prepared by the method of Wu et al. (Wu et al., 1997) and injected by a Narishige syringe microinjector to ~2% oocyte volume. For experiments using oxyhemoglobin, oocytes were injected 30 to 45 minutes prior to sperm factor injection with oxyhemoglobin to ~200 uM final heme concentration. Calcium levels were monitored as detailed above.

What is claimed is:

1. A method of activating an oocyte in vitro, the method comprising:
   injecting nitric oxide, a nitric oxide donor, nitric oxide synthase, or inducer of nitric oxide synthase into a non-activated oocyte in an amount effective to activate said oocyte; and,
   maintaining said oocyte until pronuclei have formed and migrated within the oocyte,
   wherein said activation is performed in the absence of sperm.

2. The method according to claim 1, wherein said oocyte is a mammalian oocyte.

3. The method of claim 2, wherein said oocyte is a human oocyte.

4. A method of activating an oocyte in vitro, the method comprising:
   injecting nitric oxide, a nitric oxide donor, nitric oxide synthase, or inducer of nitric oxide synthase into a non-activated oocyte in an amount effective to activate said oocyte; and maintaining said oocyte until pronuclei have formed and migrated within the oocyte.

5. The method of claim 1, wherein said injecting is microinjecting.

6. The method of claim 4, wherein said injecting is microinjecting.

* * * * *